United States Patent
Zdasiuk et al.

(10) Patent No.: US 8,350,226 B2
(45) Date of Patent: Jan. 8, 2013

(54) METHODS AND SYSTEMS FOR TREATING CANCER USING EXTERNAL BEAM RADIATION

(75) Inventors: George Zdasiuk, Portola Valley, CA (US); James Clayton, San Jose, CA (US); Josh Star-Lack, Palo Alto, CA (US); David Humber, Los Gatos, CA (US); Gary Virshup, Cupertino, CA (US); Michael C. Green, Palo Alto, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 365 days.

(21) Appl. No.: 12/572,265

(22) Filed: Oct. 1, 2009

(65) Prior Publication Data

US 2010/0102244 A1   Apr. 29, 2010

Related U.S. Application Data

(60) Provisional application No. 61/108,005, filed on Oct. 23, 2008.

(51) Int. Cl.
*H01J 1/50* (2006.01)
(52) U.S. Cl. .......... 250/396 ML; 250/492.1; 250/492.2; 250/492.3; 250/396 R; 250/505.1
(58) Field of Classification Search ........... 250/396 ML, 250/492.1, 492.2, 492.3, 396 R, 505.1
See application file for complete search history.

(56) References Cited

U.S. PATENT DOCUMENTS

| | | | |
|---|---|---|---|
| 4,598,415 A * | 7/1986 | Luccio et al. ................. 378/119 |
| 4,705,955 A | 11/1987 | Mileikowsky | |
| 4,726,046 A * | 2/1988 | Nunan ............................ 378/65 |
| 7,940,891 B2 * | 5/2011 | Star-Lack et al. ............... 378/65 |
| 2004/0149934 A1* | 8/2004 | Yanagisawa et al. ....... 250/492.3 |
| 2005/0084073 A1 | 4/2005 | Seppi et al. | |
| 2007/0242801 A1 | 10/2007 | Mackie et al. | |
| 2008/0067449 A1* | 3/2008 | Guertin et al. ............. 250/493.1 |
| 2009/0299634 A1 | 12/2009 | Schaffner | |

FOREIGN PATENT DOCUMENTS

| | | |
|---|---|---|
| JP | 10328316 | 12/1998 |
| JP | 2000-331799 | 11/2000 |

OTHER PUBLICATIONS

PCT, International Search Report and Written Opinion of the International Searching Authority in PCT/US2009/059303, Apr. 30, 2010, 12 pages.

* cited by examiner

*Primary Examiner* — Jack Berman
*Assistant Examiner* — Meenakshi Sahu
(74) *Attorney, Agent, or Firm* — Houst Consulting (57) ABSTRACT

A radiation system employs magnetic field to move particle beams and radiation sources. The radiation system includes a source operable to produce a particle beam, a scanning magnet operable to scan the particle beam, and a target configured to be impinged by at least a portion of the scanned particle beam to produce radiation.

25 Claims, 7 Drawing Sheets

METHODS AND SYSTEMS FOR TREATING CANCER USING EXTERNAL BEAM RADIATION

CROSS REFERENCE TO RELATED APPLICATIONS

This application claims the priority to U.S. Provisional Application No. 61/108,005 filed Oct. 23, 2008 entitled "Methods and Systems for Treating Cancer Using External Beam Radiation," the disclosure of which is incorporated herein by reference in its entirety.

BACKGROUND

This invention relates in general to radiation treatment of diseases and in particular to radiation systems and methods useful in diagnosis and treatment of breast cancer.

It is estimated that as many as 80% of women diagnosed with breast cancer may be eligible for breast cancer conservation (BCT) therapy. Numerous clinical trials have demonstrated that survival rates are increased if surgical removal of the tumor (lumpectomy) is followed by radiation therapy. Whole-breast external beam fractionated radiation therapy, often coupled with a boost dose to the tumor region, is now the clinically accepted standard-of-care.

Despite the high indication rate for cancer conservation therapy, many women still opt for mastectomy. This is partly due to the inconvenience of the fractionated treatment regimen which may last up to six weeks. The associated time commitment and logistical difficulties associated with daily travel may discourage a number of women from choosing cancer conservation therapy.

Accordingly, to significantly reduce the cost of treatment in general and encourage more patients to adopt cancer conservation therapy, there is a need for radiation treatment systems that require less capital equipment and infrastructure costs associated with building new treatment center closer to patients' residence. There is also a need for radiation therapy that requires reduced number of treatment fractions. Research into accelerated partial breast irradiation using interventional techniques such as MammoSite® has shown some promise. This has spurred encouraging investigations into hypo-fractionation using external beams such as intensity-modulated radiation therapy (IMRT).

SUMMARY

A radiation system includes a source operable to produce a particle beam, a scanning magnet operable to scan the particle beam, and a target configured to be impinged by at least a portion of the scanned particle beam to produce radiation. In a preferred embodiment, the scanned particle beam can be transported in two or more beam paths, and at least one bending magnet is provided in at least one of the beam paths to turn at least the scanned particle beam toward the target.

In some embodiments, the scanning magnet comprises a first scanning magnet operable to scan the particle beam in a first direction and a second scanning magnet operable to scan the particle beam in a second direction, whereby a beam moving in a generally circular path is formed when in an operation. A bending magnet may be used to further bend the beam inward toward the target. Alternatively, a reflection target may be used to produce radiation reflected inward toward the body to be treated.

In some embodiments, the target may include a target plane. A collimator having arrays of through holes may be coupled to the target plane and configured to pass radiation traveling on straight lines with the through holes.

In some embodiments, a radiation system includes one or more particle sources operable to produce particle beams in a radial path, and one or more targets arranged in a radial path configured to produce radiation when impinged by the particle beams. The particle source may include a metallic filament in a circular configuration, or plurality of metallic filaments arranged in a circular configuration, or a cathode head. The targets may include transmission targets situated within the radial path of the particle sources, or reflection targets situated outside the radial path of the particle sources.

In some aspects, a radiation method includes the steps of producing a particle beam, scanning the particle beam, producing radiation using at least a portion of the scanned particle beam, and irradiating a body using at least a portion of the radiation produced. The radiation method may further include the step of bending the scanned particle beam prior to the step of producing radiation. The particle beam may be concurrently scanned in two directions to form a beam in a generally circular path or other 2D patterns.

BRIEF DESCRIPTION OF THE DRAWINGS

These and various other features and advantages will become better understood upon reading of the following detailed description in conjunction with the accompanying drawings and the appended claims provided below, where:

DETAILED DESCRIPTION OF VARIOUS EMBODIMENTS

Various embodiments of radiation systems are described. It is to be understood that the invention is not limited to the particular embodiments described as such may, of course, vary. An aspect described in conjunction with a particular embodiment is not necessarily limited to that embodiment and can be practiced in any other embodiments. It is also to be understood that the terminology used herein is for the purpose of describing particular embodiments only, and is not intended to be limiting since the scope of the invention will be limited only by the appended claims, along with the full scope of equivalents to which such claims are entitled.

In addition, various embodiments are described with reference to the figures. It should be noted that the figures are not drawn to scale, and are only intended to facilitate the description of specific embodiments. They are not intended as an exhaustive description or as a limitation on the scope of the invention.

All technical and scientific terms used herein have the same meaning as commonly understood by one of ordinary skill in the art to which this invention belongs, unless defined otherwise. Various relative terms used in the description or appended claims such as "above," "under," "upper," "over," "on," top," "bottom," "higher," and "lower" etc. are defined with respect to the conventional plane or surface being on the top surface of the structure, regardless of the orientation of the structure, and do not necessarily represent an orientation used during manufacture or use. The following detailed description is, therefore, not to be taken in a limiting sense. As used in the description and appended claims, the singular forms of "a," "an," and "the" include plural references unless the context clearly dictates otherwise.

Patient Orientations and Supporting Structures

In general, a body such as a patient to be treated can be in any suitable position supported by a structure. As illustrated in FIGS. 1-9, the structure 102 may function to support a body in a suitable orientation and protect healthy parts of the body from unnecessary irradiation. The structure 102 may be further configured to position and/or immobilize the body, or physically protect the body from moving parts. The structure 102 can be an integral part of a housing configuration in which a radiation device is placed. The structure 102 may also be in the form of a table on which a patient is supported.

In some preferred embodiments for radiation therapy and/or imaging of cancer, the structure 102 can be provided with an opening to allow a portion of the body such as a patient's breast passing through. The opening provided in the structure 102 can be configured in circular shape, or in other regular or irregular shape to allow for example, a breast, and/or the axillary tissue passing through. The opening may be provided in a removable portion in the structure 102 such that the opening may be readily customized for patients with breasts of different sizes, or for different body portions such as the breast and its axillary tissue. The removable portion may also be used for other purposes such as for calibrating the radiation device. In some preferred embodiments, a structural member such as a holder or cup or the like can be coupled to the structure for receiving, supporting, or confining a body portion to be treated. For example, the structural member can be a hollow cylinder defining a treatment region in which a body portion is to be treated.

The structure 102 may have various configurations suitable for supporting a patient in suitable positions or orientations, such as lying, lying side way, standing, seating, and leaning positions. In some preferred embodiments, the structure 102 may be configured to support a patient in prone or nearly prone position to allow a body portion such as a patient's breast to extend through an opening in the structure while the rest of the body is shielded by the structure walls. The prone or quasi-prone positions are desirable in minimizing breast motion due to breathing while also reducing radiation exposure to organs at risk. Ultimately, the determination of which orientations is optimal will depend upon clinical issues related to treatment efficacy, side effects and patient comfort.

The structure 102 may be constructed with any suitable materials that absorb radiation. Suitable radiation absorbing materials are known in the art, which include, but are not limited to: lead, tungsten, tantalum, uranium, thorium, iridium, gold, iron, aluminum, and their alloys or mixtures or in binders that contain them including glass, plastic, and sheet rock. Near the region of the patient's breast or body portion, the structure 102 may be constructed with materials that have lower radiation absorption to allow penetration of the radiation to areas of interest such as the chest wall of the patient.

Figure 1:
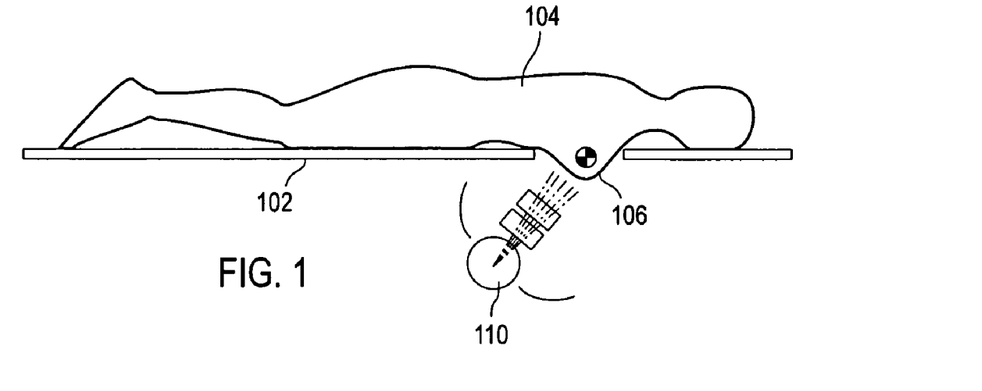
FIG. 1 is a side view illustrating a patient supported by a structure in a prone position in accordance with some embodiments.
Figure 2:
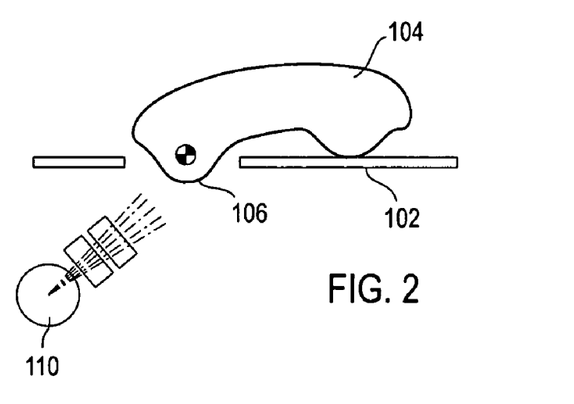
FIG. 2 is a front view illustrating a patient supported by a structure in a prone position in accordance with some embodiments.
Figure 3:
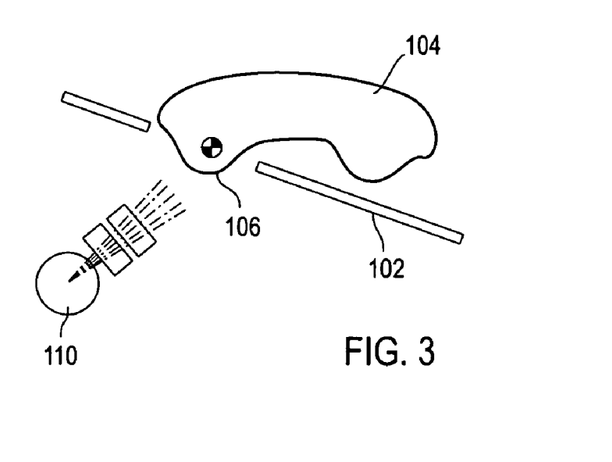
FIG. 3 is a front view illustrating a patient supported by an angled structure in a prone position in accordance with some embodiments.

FIGS. 1-3 illustrate some exemplary structures 102 and orientation of a patient supported by the structures. A prone or nearly prone patient 104 is supported by structure 102 with the ipsilateral breast 106 in a pendulous position extending nearly or substantially vertically through an opening 108 into a radiation device 110. The device 110 is situated underneath the structure 102 and moves about the breast 106 to generate multiple treatment fields. The structure 102 may have a flat or domed surface in the cranial-caudal direction with the peak of the arc located in the chest region to provide comfort. The structure 102 may be rolled or angled to reduce pressure on the contra-lateral breast (FIG. 3). The structure 102 may also have a recess 112 (FIG. 4) such that when a patient is positioned in the recess the treatment head of a device can be raised above the plane of the breast on one side of the patient. The recess geometry may provide a tangential view and improved access to the lymph nodes and axilla for treatment and imaging.

U.S. patent application Ser. No. 12/256,461 filed Oct. 22, 2008 discloses various embodiments of structures supporting patients in various orientations in conjunction with an X-ray source for radiation treatment and imaging, the disclosure of which is incorporated herein by reference in its entirety.

Means for Transporting, Bending, and Moving Charged Particle Beams to Treat Breast Cancer, Cancers of the Head and Neck, and Other Cancers In some embodiments, the present invention provides a radiation system where magnetic fields are used to provide much of the motion of particle beams around a body to be examined. The mechanical motions that are needed to move particle beam sources are much less complicated than for conventional systems. In some cases only partial rotation, tilting, or a motion that can change the elevation and an X-Y stage are needed. As used herein, a charged particle beam refers to a beam of electrons, protons, heavy ions, or other charged particles.

Figure 4A:
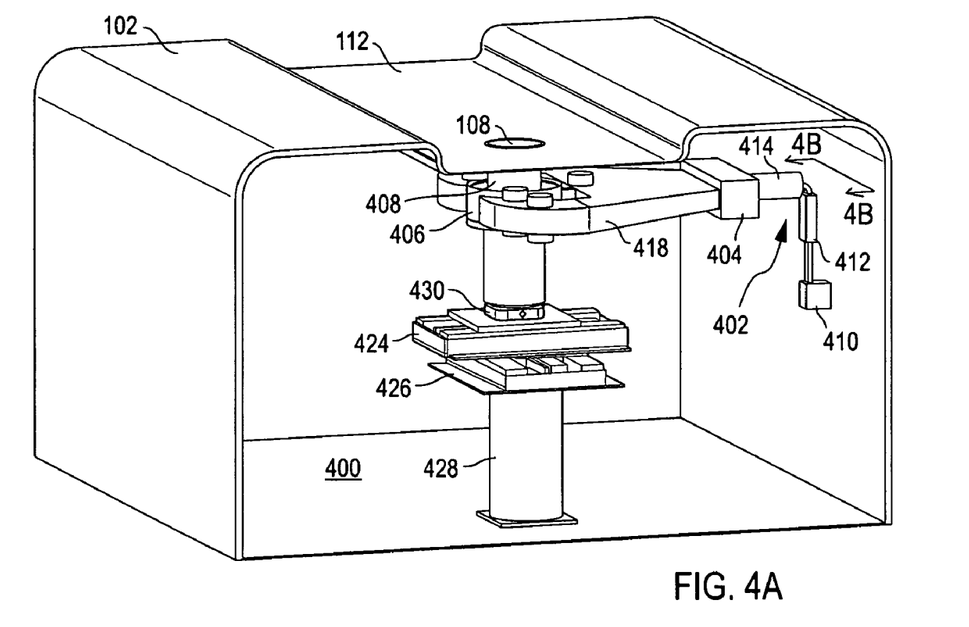
FIG. 4A is a perspective view illustrating an exemplary radiation system including a scanning magnet in accordance with some embodiments.
Figure 4B:
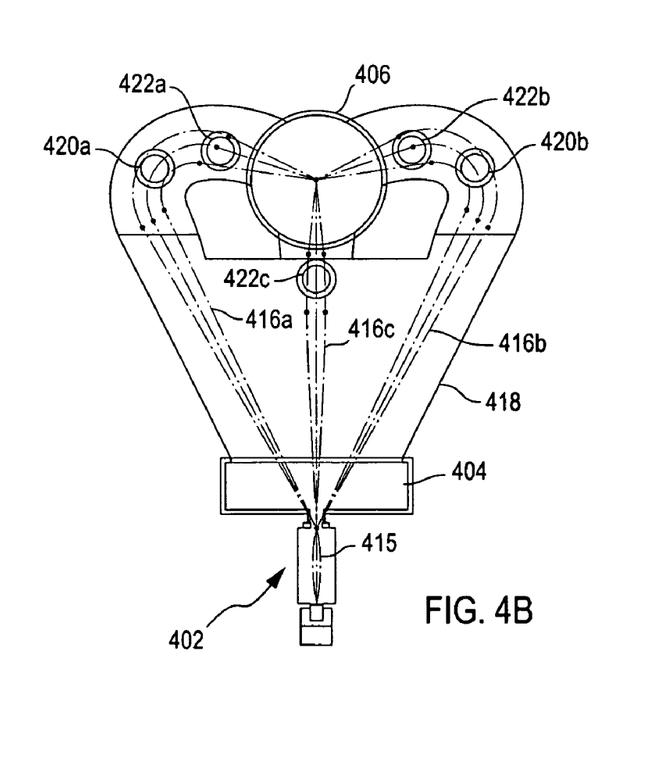
FIG. 4B is a cross sectional view taken along lines 4B-4B of FIG. 4A.

FIGS. 4A and 4B illustrate an exemplary radiation system 400. Generally, the radiation system 400 includes a particle source 402 operable to produce charged particle beams, and a scanning magnet 404 operable to scan or transport the particle beams. In some embodiments, the scanned particle beams are delivered to a target 406 configured to produce radiation directed to a body adjacent to the target 406. In some embodiments, the scanned particle beams are delivered directly to a body or body portion to be treated. In some embodiments, the scanned particle beams are further bent before being delivered to the body to be treated. The body or body portion to be treated can be positioned in a region defined by a member 408 such as a cylinder, a cup, or the like. For illustrative purposes, the radiation system 400 is shown in conjunction with an enclosed structure 102 having a recess geometry that is configured to support a patient in a prone position. It will be appreciated that the system 400 can be used in conjunction with structures in other suitable geometry or configuration to support a patient in a variety of orientations or positions as described above.

The particle source 402 can be either a linear accelerator or an X-ray tube. By way of example, an X-band Clinac operable to produce electron beams with an energy level ranging from 1 to 4 MV can be used as a particle source 402. Other sources operable to produce other charged particle beams can also be used. The present invention is not limited to a particular particle source or beam with a particular energy level. As shown in FIG. 4A, a linear accelerator 402 may include a microwave source 410 such as magnetron, a waveguide 412, and a head unit 414. The head unit 414 may include an electron gun and an accelerator guide. In operation, the electron gun is activated to emit electrons, which are accelerated by the accelerator guide. The acceleration of electrons can be controlled by microwaves which are generated by the microwave source 410 and supplied via the waveguide 412. One or more rotary waveguide joints can be used to allow the waveguide 412 to extend its length down from an arm. Rotary waveguide joints enable the accelerator head unit 414 to be mounted proximate to the very end of an arm, and allows a heavy microwave source 410 such as a klystron and other heavy RF components to be mounted relatively remotely from the head unit 414 such as on the ground, or distributed along an arm. U.S. patent application Ser. No. 12/256,461 filed Oct. 22, 2008 discloses a radiation system using robotic arms and rotary waveguide joints, the disclosure of which is incorporated herein by reference in its entirety.

The scanning magnet 404 operates to scan the particle beam or move the beam into at least two separate beam paths using e.g. a time varying magnetic field. FIG. 4B shows that a particle beam 415 produced by a particle source 402 is scanned by the scanning magnet 404 into three beam lines 416a, 416b, 416c. It should be appreciated that the particle beam can be split or scanned into different number of beam lines depending on applications. The scanned beam drifts or travels in a vacuum chamber 418 or a number of vacuum chambers each for one of the beam lines. Additional magnetic or electronic means may be provided in the vacuum chamber or chambers 418 to further shape or deflect the particle beams. For example, in some preferred embodiments, bending magnets such as dipole bending magnets 420a, 420b can be used to bend the particle beams 416a, 416b, turning the beams in trajectories towards a target 406 or towards the body portion to be treated. Alternatively, the particle beam such as beam 416c may travel directly to a target 406 or to the body portion without the need for further bending or focusing. Focusing magnets 422a, 422b, and 422c may be disposed in the beam path to adjust the shape of the particle beams or to increase or decrease the size of the particle beam.

X-ray target or targets 406 are located adjacent to the body to be treated and configured to produce radiation when impinged with particle beams. By way of example, the target or targets 406 may be attached to an end wall of the vacuum chamber 418. Either reflection targets or transmission targets may be used. The target 406 may be a single target, a plurality of targets, or a continuous target plane. For example, a target or targets may be support by or deposited on a structure member having a circular, triangular or other regular or irregular shape surrounding the treatment region. Depending on the energy of the particle beam, about 0.5-25 percent of the particles can be converted into X-rays. A collimator can be used to adjust the shape of the radiation produced and aimed at the body to be treated. Various targets or collimators are available from Varian Medical Systems, Inc. (Palo Alto, Calif.).

Various stages may be optionally provided to translate, rotate, or support the radiation system 400. For example in FIG. 4A, stages 424, 426 may be used to translate or adjust the position of the radiation source in X- or Y-directions. Vertical stage 428 may be used to raise or lower the radiation source along the Z-axis. Rotary stage 430 may be used to rotate the radiation source around a vertical axis. The design of vertical or X-Y stages are much less complicated, and their movement can be more accurately controlled. In radiation system 400, magnetic fields provide much of the motion of the particle beams and thus the motion of the radiation sources around the body treated.

For systems using beam scanning, a design consideration concerns the magnetics required to steer and focus the particle beam. Generally dipole magnets can be used to steer beams in X-Y directions, and focusing solenoids or quadrupole magnets can be used to adjust the shape. Higher order magnetic multipoles can be used to address achromatic effects if required. The magnetic currents can be dynamically calibrated and adjusted so that the position and shape of the beam can be programmed. One method of obtaining feedback about an electron beam profile and position is to use wire sensors placed in the target region. As the beam interacts and moves across a specific wire, an electric current is produced which can be used to derive the beam shape and position. This information can be fed back into a control system. Another method is to use an imaging device that measures X-ray flux coupled with collimators arrayed around the target. Beam position and shape can be derived from X-ray images and the information fed back into a control system. In either case, the control does not have to be real time. Another method is to use the fact that the beam will induce a charge on a conductor as it passes inside a cylinder. This cylinder can be segmented into quadrants for example and the values of the charge induced can be read out. Comparator circuitry and computer algorithms can be used to dynamically tune the beam to the desired locations. Also higher order multipole magnets such as sextapoles may also be used to address achromatic and aberration effects.

Figure 5A:
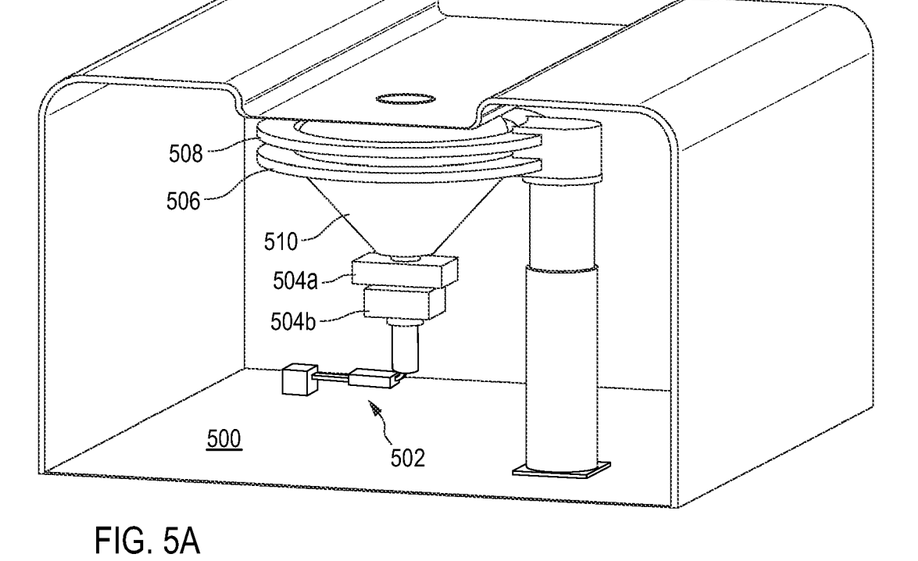
FIG. 5A is a perspective view illustrating an exemplary radiation system including X-Y scanning magnets in accordance with some embodiments.
Figure 5B:
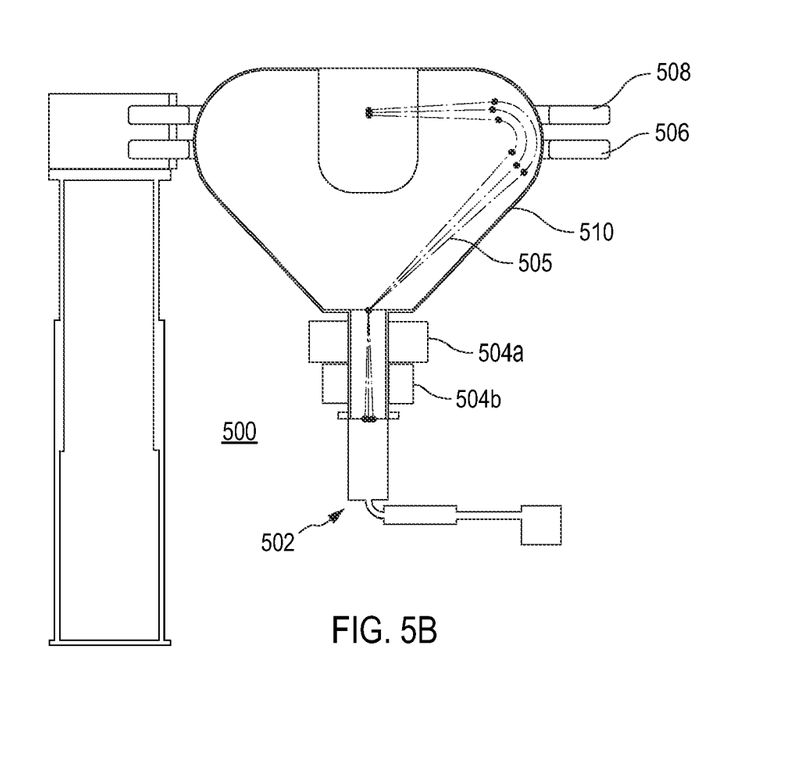
FIG. 5B is a cross sectional view taken along lines 5B-5B of FIG. 5A.

FIGS. 5A-5B illustrate another exemplary radiation system 500 in accordance with some embodiments of the present invention. The radiation system 500 includes a particle source such as a linear accelerator or X-ray tube 502 operable to produce charged particle beams, and a pair of scanning magnets or coils 504a, 504b. The pair of scanning magnets 504a, 504b are operable to scan a particle beam in two directions such as in X- and Y-directions, making the beam 505 to move or orbit in a generally circular path.

In some embodiments, a bending magnet such as a dipole magnet 506 may be used to further bend the particle beam 505. The particle beam 505 may be further bent about 90 or 270 degrees such that the beam turns and directs to a target or a treatment region. A focusing magnet 508 may be used to focus or adjust the shape of the beam. By way of example, if the kinetic energy of the incident electrons is about 1 MeV, it would have a bend radius of about 0.31 cm if the magnetic field is about 1.5 T (15 kG). This field level can be achieved with iron core magnets and modern solid state amplifiers.

Other materials can also be used which can generate even higher magnetic fields to further reduce the radius. The beam would then be roughly cylindrical around the treatment region. This would enable a method to create a volumetric arc therapy treatment plan with the most of the motion being accomplished with electronics via time varying magnetic fields. Generally the rates for such scanning can be at least 100 Hz and are limited to no more than a few KHz. This is due to eddy current heating and ability to drive the inductive loads of the magnetic coils from maximum positive to maximum negative values. This could be done with kilovoltage energies or with megavoltage energies. Non-coplanar treatments are possible with these systems. In some embodiments, the particle source 502 may be provided with a control grid to quickly turn off and on the beam, or skipping portions of the scan.

In some embodiments, the beam 505 passing the scanning magnets 504a, 504b is not further bent 90 or 270 degrees as described above. Instead, the beam 505 may impinge reflection targets to produce X-ray radiation. The reflection targets may be mounted to the outer wall of the vacuum chamber 510 and may be cooled by air or water or other fluids. The targets may point inwards towards the treatment region and may be situated preferably at angles ranging from 4 to 15 degrees relative to a vertical axis. By way of example, rings of targets spanning 360 degrees or a subset of 360 degrees may be used to provide sufficient axial and transaxial coverage to irradiate the body to be treated. The targets may be staggered in a way such that the back of each can be individually cooled.

Figure 6A:
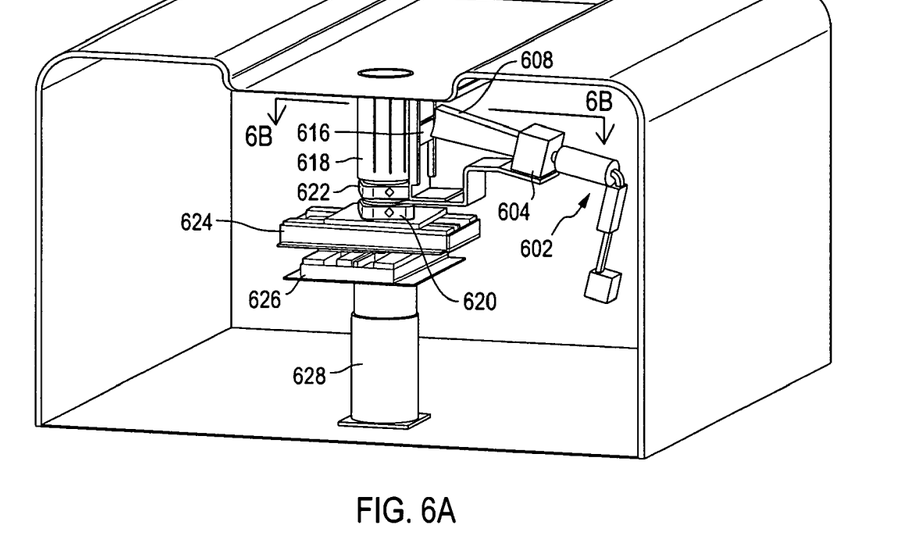
FIG. 6A is a perspective view illustrating an exemplary radiation system including a scanning magnet in accordance with some other embodiments.
Figure 6B:
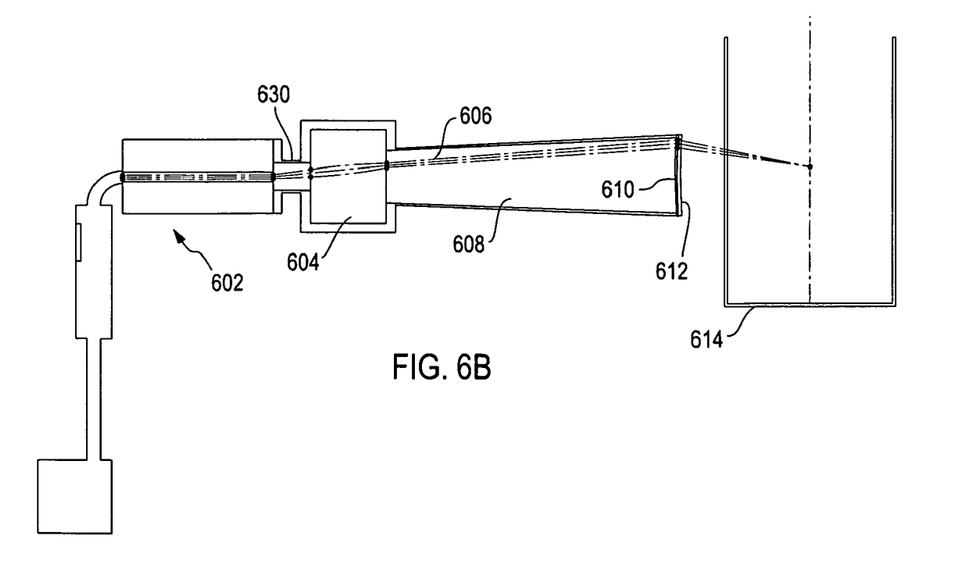
FIG. 6B is a cross sectional view taken along lines 6B-6B of FIG. 6A.

FIGS. 6A-6B illustrate a further exemplary radiation system 600 in accordance with some embodiments of the invention. The radiation system 600 includes a particle source such as a linear accelerator or X-ray tube 602 operable to produce charged particle beams, and a scanning magnet or coils 604 operable to scan the particle beams from the particle source 602. The scanned beam 606 travels in a vacuum chamber 608 and strikes a target plate 610 disposed proximate to an end of the vacuum chamber. Radiation is produced, collimated, and directed to the treatment region 614.

The target 610 may be constructed with a parallelepiped tungsten or other high density materials. The target 610 may be attached to or deposited on a backing plate. The thickness of the high density target can range from about ⅓ to ½ in length (or depth i.e. m or cm) or the electron range in the material. The backing plate can be constructed with copper, a copper alloy, beryllium, or other metals or metal alloys to stop electrons. The backing plate may be provided with channels for circulating cooling fluid to dissipate heat generated during operation. For the high power targets water cooling or some other cooling fluid can be used. The target can be either brazed to the backing plate or deposited by chemical vapor deposition (CVD), physical vapor deposition (PVD), electroplating or other means of attachment with high thermal conductivity. In some embodiments, the electrons may be on the order of 1 MeV in kinetic energy and they strike a target that may be made of several layers. By way of example, a tungsten target may have a thickness between 0.001" and 0.01" and a copper backing plate may have a thickness on the order of 0.020-0.040". The braze material may be an alloy of cooper, nickel and gold etc. on the order of 0.001-0.003" in thickness. The exact ratios and materials can be determined based on end applications without undue experimentation.

The collimator 612 coupled to the target plate 610 can be a fixed collimator constructed with a plate or series of plates of tungsten or other high density material that can attenuate X-rays with minimal thickness. A series of through holes may be provided in the collimator plate to permit X-rays to exit the collimator and illuminate the treatment region. The length, spacing, or pattern of the through holes can be configured to pass X-rays that are straight lines with the through holes. Radiation that is oblique to the through holes is absorbed by the collimator materials. Thus, the selection of which regions of the target plane are illuminated generally determines the collimation of the beam. This in conjunction with the field of view of the collimated holes then determines the collimation of the treatment beam. Alternatively, collimators with movable leaves known in the art can be used.

The particle beam 606 can be scanned such that the beam is moved across the target plate 610 in either horizontal or vertical lines. The beam 606 can be continuously moved along predetermined scan-lines over the target plate (raster scan). Alternatively, the beam 606 may be switched off and on in a predetermined time interval when moving from one spot to another (spot scanning). In the case of raster scanning, the velocity of the beam may be controlled to adjust the radiation dose. In the case of spot scanning, the spot dwelling time may be controlled to adjust the radiation dose.

In some embodiments, the target 610 can be in the form of a strip so that the particle beam 606 is only scanned in one direction and the beam collimation is moved in an up and down or side to side motion. Focusing collimators such as horizontal collimator 616 and/or vertical collimators 618 may be used in conjunction with the target 610 (FIG. 6A). The focusing collimators 616 or 618 may be provided with moving capabilities via rotary or linear stages. Alternatively, collimators with moving leaves can be used and synchronized with the beam motion so that the X-rays are like a moving focal spot. The shape of the beam can be modulated by changing the shape of the collimator leaves. The beam spots can be then conformal to the projection size of the tumor. With this system conformal treatments can be achieved.

The radiation system 600 with an extended target strip can also be used in cargo screening to decrease the source to detector distance. The typical source to detector distance in cargo screening ranges from about 5 to 12 meters. With a scanning system of the present invention, the source to detector distance can be reduced to about 3-6 meters. This has advantages that the throughput can be increased as one would have a higher output radiation system. There would be no need for detector compromises with energy varying X-ray yield as one currently has with conventional accelerator based X-ray scanners. With a reduced footprint, the shielding can be reduced since the source is closer to the object and detectors. The scanning system 600 can also be used to scan large objects such as pressure vessels, gas turbine blades and missiles. This technology would make these inspections happen more quickly and accurately.

The radiation system 600 may be provided with the capability of rotation or translation via rotary stages 620, 624, or X-, Y-, or Z-stages 624, 626, 628 (FIG. 6A). In some embodiments, rotating vacuum joints such as a Ferrofluidic coupler 630 may be used to permit rotation of the beam line (FIG. 6B). The use of rotating vacuum joints 630 provides additional capability of motion via X-Y stages and a vertical stage. Tilting capability can also be provided. With this type of system an achromatic beam transport system can be built using a slalom type of magnet arrangements that achromatically transport the beam to the target. The final bend can be a full 270 degree bend. With this system if all degrees of freedom are implemented then 5 degrees of freedom would be provided. Beam scanning in the vertical direction can also be accomplished.

In some embodiments, the present invention provides a radiation system where a particle source is arranged or plurality of particle sources are arranged in a radial path. Particle beams are produced and directed inward from the radial path in operation. Targets are positioned adjacent to the particle source or sources to produce radiation when impinged by the particle beams. The radiation produced is collimated and delivered to a body positioned within the radial path. Bending magnets, scanning magnets, or electrostatic deflectors may be used to move the electron beam.

Figure 7A:
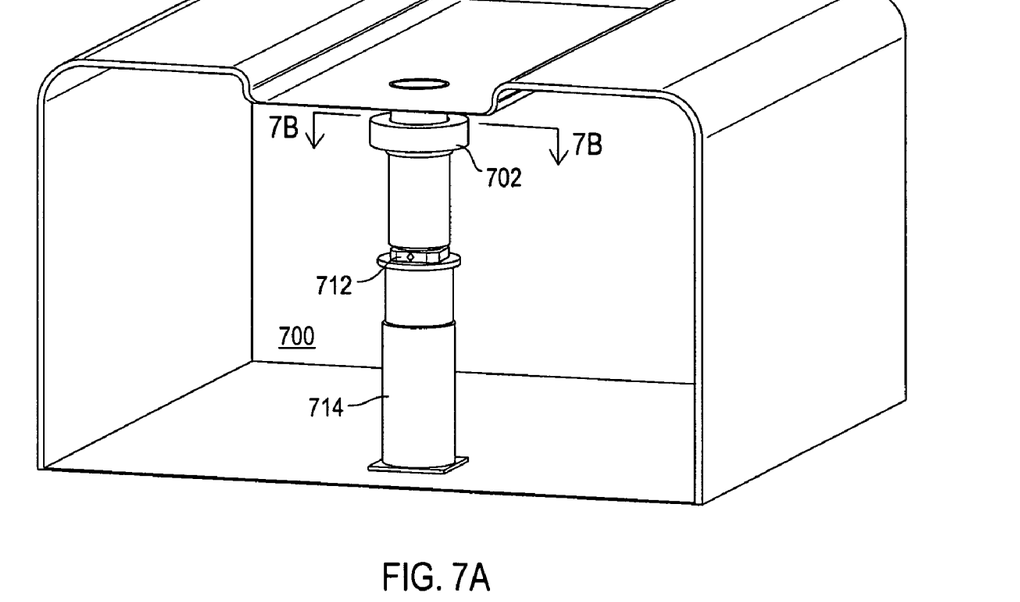
FIG. 7A is a perspective view illustrating an exemplary radiation system including a radial filament tube in accordance with some embodiments.
Figure 7B:
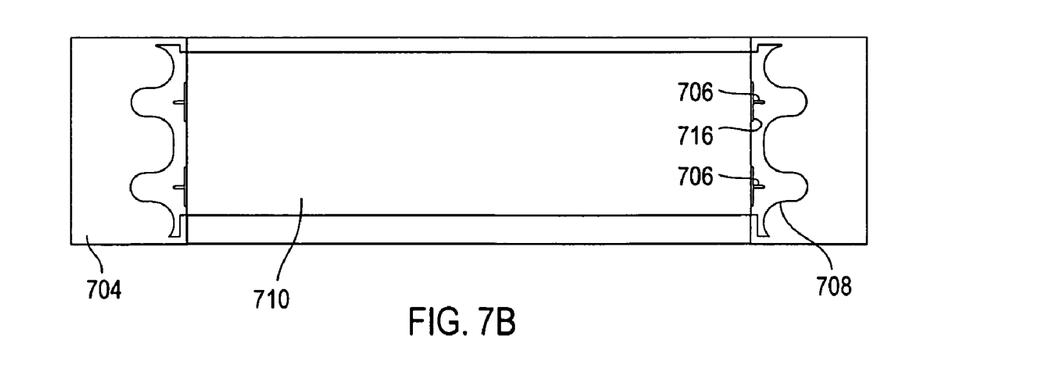
FIG. 7B is an enlarged cross sectional view taken along lines 7B-7B of FIG. 7A.

FIGS. 7A-7B illustrate an exemplary radiation system 700 in which a radial filament tube 702 is used. The filament tube 702 may include a vacuum chamber 704 and one or more metallic filaments 706 as particle or electron sources. The one or more metallic filaments 706 may be situated in an electron focusing housing 708. Window 710 such as a beryllium window allows radiation passing through to a body to be treated. The radial filament tube 702 may be rotated or translated via rotary stage 712 or linear stage 714.

The metallic filament(s) 706 may be a continuous wire such as tungsten or other metallic wire folded in an arc or a full circle, or a plurality of segments arranged in an arc, a full circle of 360 degrees, or a subset of full 360 degrees. The filament(s) 706 or electrodes are arranged so that particles or electrons start on a radial path and are directed inward to a target or targets 716 surrounding a body to be treated. The electrons strike the target 716 and create Bremsstrahlung X-rays, which can be collimated via fixed holes in a collimator coupled to the target or targets. Alternatively, a collimator can move in a circular pattern that is synchronized with the filaments that are being addressed. Additional control to the filament 706 or beam circuitry can be accomplished by adding a control grid that can turn the beam off or on. In the case of the segmented filament, the filaments can be left on and the electron flow is determined by the voltage on the segmented grid. In this way the beam spot location, duration in time, or intensity can be controlled.

Figure 8A:
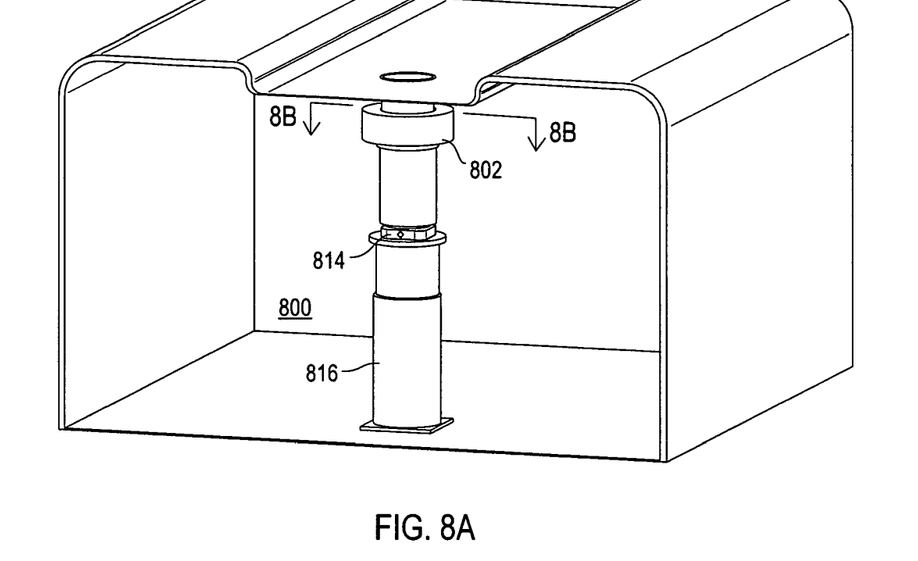
FIG. 8A is a perspective view illustrating an exemplary radiation system including a radial cathode head tube in accordance with some embodiments of the invention.
Figure 8B:
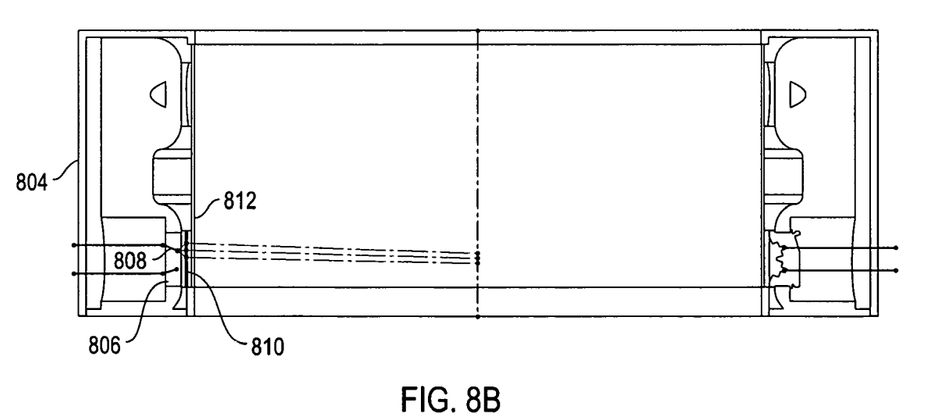
FIG. 8B is an enlarged cross sectional view taken along lines 8B-8B of FIG. 8A.

FIGS. 8A-8B illustrate an exemplary radiation system 800 in which a radial cathode head tube 802 is used. The cathode head tube 802 may include a vacuum housing 804 and a plurality cathode heads 806 arranged in a radial path. Each of the cathode heads 806 may include one or more metallic filaments 808 as particle or electron sources. Target and collimator coupled to the target (collectively 810) are located adjacent to the cathode heads 806. Electrons start on a radial path and are directed inward to the target 810. Radiation produced is collimated, and passes through window 812, and is directed inward to a body surrounded by the target/collimator 810. Control of the cathode heads 806 or filaments 808 can be accomplished by a control grid or beam circuitry. The cathode head tube 802 may be rotated or translated via rotary stage 814 or linear stage 816.

Figure 9A:
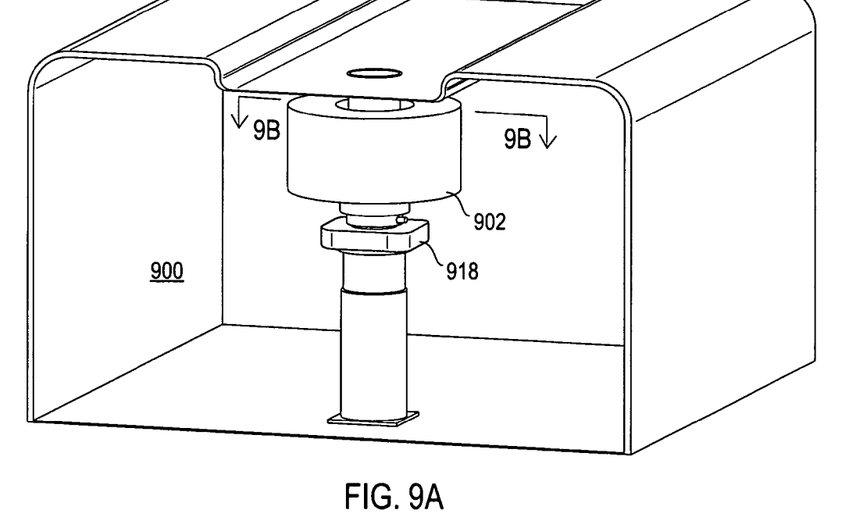
FIG. 9A is a perspective view illustrating an exemplary radiation system including an angular tube in accordance with some embodiments.
Figure 9B:
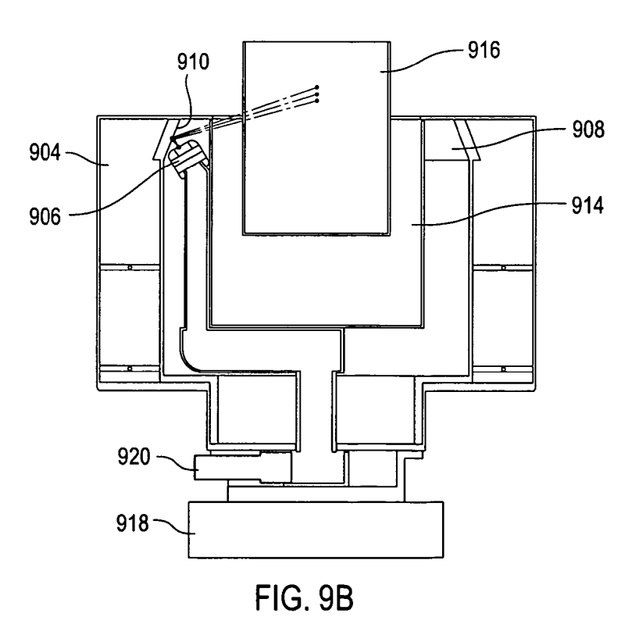
FIG. 9B is an enlarged cross-sectional view taken along lines 9B-9B of FIG. 9A.

FIGS. 9A-9B illustrate an exemplary radiation system 900 in which an angular tube 902 is used. The angular tube 902 may include a vacuum chamber 904, a cathode head 906, and a target 908. The target 908 is preferably a reflection target supported on a rotating anode 910. The target 908 can be situated at an angle ranging e.g. from 4 to 15 degrees relative to a vertical axis. The cathode head 906 is preferably positioned such that electrons emitting from the cathode head 906 are directed to the target 908 at an angle, producing radiation that directs inward toward a treatment region surrounded by the rotating target 908. Radiation 912 may be collimated, passes through window 914, and directed toward a treatment region 916. The tube 902 may be rotated via a rotary stage 918. Cable 920 electrically connects the cathode head 906 to a control circuit.

Various embodiments of a radiation system have been described. The system can be advantageously constructed with small form factors and self-contained. The system may be largely self-shielded. A patient may lie prone or quasi-prone to facilitate self-shielded design configuration, or minimize breathing motion. The particle source may be constructed in reduced size and cost compared to that of traditional Clinac. The radiation system has the capabilities to support advanced treatment schemes such as Rapid ARC, IMRT and/or arc therapy to optimize dose distributions. This allows for minimization of skin dose, delivery of boost dose to tumor region, and hypo-fractionation. On-board imaging capabilities may be provided with the system for patient positioning and targeting, and treatment planning. The system can be specially constructed with more advanced capabilities for treating breast cancer or other cancer with reduced exposure to organs at risk.

It will be appreciated that, although specific embodiments of the invention have been described herein for purposes of illustration, various modifications may be made without deviating from the spirit and scope of the invention. All the modifications are contemplated by the invention.

What is claimed is:

1. A radiation system comprising:
    a source operable to produce a particle beam;
    a scanning magnet operable to scan the particle beam to allow the particle beam to travel in two or more paths;
    at least one bending magnet operable to bend the particle beam in at least one of the two or more beam paths; and
    a target configured to be impinged by at least a portion of the particle beam from the two or more paths to produce radiation,
    wherein the target is positioned adjacent to and configured to surround a body portion to be irradiated.

2. The radiation system of claim 1 wherein the scanning magnet is configured to scan the particle beam in a plane, and the at least one bending magnet is configured to bend the particle beam in the plane.

3. The radiation system of claim 1 wherein the particle source comprises a linear accelerator operable to produce an electron beam having an energy level ranging from about 1 to 4 MV.

4. A radiation system comprising:
    a source operable to produce a particle beam;
    a scanning magnet assembly operable to scan the particle beam, wherein said scanning magnet assembly comprises a first scanning magnet operable to scan the particle beam in a first direction and a second scanning magnet operable to scan the particle beam in a second direction, whereby forming a beam moving in a generally circular path when in an operation; and
    a target configured to produce radiation when impinged by the particle beam, wherein the target is positioned adjacent to and configured to surround a body portion to be irradiated.

5. The radiation system of claim 4 further comprising a bending magnet operable to turn the beam moving in the generally circular path inward toward the target.

6. The radiation system of claim 5 wherein the bending magnet is operable to turn the beam moving in the generally circular path inward at about 90 or 270 degrees.

7. The radiation system of claim 4 wherein the target comprises a reflection target configured to be impinged by the beam moving in the generally circular path to produce radiation reflected inward.

8. A radiation system comprising:
    a source operable to produce a particle beam;
    a scanning magnet operable to scan the particle beam; and a target configured to produce radiation when impinged by the scanned particle beam directly, wherein the target comprises a target plane, and the radiation system further comprises a collimator coupled to the target plane, said collimator having arrays of through holes configured to pass radiation traveling on straight lines with the through holes.

9. The radiation apparatus of claim 8 wherein the scanning magnet is operable to move the particle beam across the target plane of target materials in a raster pattern.

10. The radiation apparatus of claim 8 wherein the scanning magnet is operable to move the particle beam in a spot dwelling pattern.

11. The radiation apparatus of claim 8 wherein the source and the scanning magnet are rotatable relative to the target.

12. A radiation system comprising:
a plurality of particle sources arranged in a radial path configured to produce particle beams; and
a plurality of targets arranged in a radial path configured to produce radiation when impinged by the particle beams.

13. The radiation system of claim 12 wherein the plurality of particle sources comprise a metallic filament in a circular configuration.

14. The radiation system of claim 12 wherein the plurality of particle sources comprise a plurality of metallic filaments arranged in a circular configuration.

15. The radiation system of claim 12 wherein the plurality of particle sources comprise a cathode head.

16. The radiation system of claim 12 wherein the targets are situated within the radial path of the particle sources and comprises transmission targets.

17. The radiation system of claim 12 wherein the targets are situated outside the radial path of the particle sources and comprises reflection targets.

18. A radiation method comprising the steps of:
producing a particle beam;
scanning the particle beam to allow the particle beam to travel in two or more paths;
bending the particle beam in at least one of the two or more paths;
producing radiation using at least a portion of the particle beam from the two or more paths to impinge a target, wherein the target is positioned adjacent to and configured to surround a body portion to be irradiated; and
irradiating the body portion using at least a portion of the radiation produced from two or more directions.

19. The radiation method of claim 18 wherein the particle beam is scanned in a plane, and the particle beam in the at least one of the two or more paths is bent in the plane.

20. The radiation method of claim 18 wherein the body portion is an uncompressed breast of a patient in a prone position.

21. A radiation system comprising;
a source operable to produce a particle beam;
one or more scanning magnets operable to scan the particle beam such that the particle beam travels in two or more paths in a plane; and
one or more bending magnets in at least one of the two or more paths operable to bend the particle beam in the plane, whereby a body is irradiated from two or more directions.

22. The radiation system of claim 1 wherein the source is operable to produce electron beams.

23. The radiation system of claim 1 wherein the target is configured to encircle a treatment region within which a body portion can be positioned for irradiation.

24. The radiation system of claim 12 wherein the plurality of particles sources are configured to produce electron beams.

25. The method of claim 18 wherein said particle beam is an electron beam.

* * * * *